United States Patent
Tsaur

(10) Patent No.: US 6,903,057 B1
(45) Date of Patent: *Jun. 7, 2005

(54) PERSONAL PRODUCT LIQUID CLEANSERS STABILIZED WITH STARCH STRUCTURING SYSTEM

(75) Inventor: Liang Sheng Tsaur, Norwood, NJ (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/849,627

(22) Filed: May 19, 2004

(51) Int. Cl.$^7$ .................................. A61K 7/00
(52) U.S. Cl. ................. 510/130; 510/156; 510/424; 510/462; 510/474; 424/70.1
(58) Field of Search ............................... 510/130, 156, 510/424, 462, 474; 424/70.1

(56) References Cited

U.S. PATENT DOCUMENTS

| | | |
|---|---|---|
| 3,580,853 A | 5/1971 | Parran, Jr. |
| 5,085,857 A | 2/1992 | Reid et al. |
| 5,308,526 A | 5/1994 | Dias et al. |
| 5,439,682 A | 8/1995 | Wivell et al. |
| 5,661,189 A | 8/1997 | Grieveson et al. |
| 5,700,455 A * | 12/1997 | Hinterwaldner et al. . 424/70.14 |
| 5,854,293 A | 12/1998 | Glenn, Jr. |
| 5,905,062 A | 5/1999 | Elliott et al. |
| 6,001,344 A | 12/1999 | Villa et al. |
| 6,172,019 B1 | 1/2001 | Dehan et al. |
| 6,248,338 B1 * | 6/2001 | Muller et al. ................ 424/401 |

FOREIGN PATENT DOCUMENTS

| | | |
|---|---|---|
| WO | 92/18100 | 10/1992 |
| WO | 94/03152 | 2/1994 |
| WO | 97/48378 | 12/1997 |

OTHER PUBLICATIONS

U.S. Appl. No. 10/849,100, filed May 19, 2004, Tsaur et al., Personal Product Liquid Cleansers Combined Fatty Acid and Water Soluble or Water Swellable Starch Structuring System.

U.S. Appl. No. 10/849,408, filed May 19, 2004, Zhang et al., Soap Bars Comprising Synergestically High Levels of Both Free Fatty Acid and Filler.

* cited by examiner

Primary Examiner—Necholus Ogden
(74) Attorney, Agent, or Firm—Ronald A. Koatz

(57) ABSTRACT

The invention relates to liquid cleansers which comprise water soluble or water swellable starch to structure the composition.

12 Claims, No Drawings

PERSONAL PRODUCT LIQUID CLEANSERS STABILIZED WITH STARCH STRUCTURING SYSTEM

FIELD OF THE INVENTION

The present invention relates to personal product, liquid cleansing compositions containing novel structuring system for stabilizing (e.g., preventing phase separation) skin benefit agent (e.g., emollient and/or particles) in said compositions. In particular, the compositions provide good consumer desirable properties (e.g., lathering, non-stringy, non-lumpy appearance) while maintaining good stability (e.g. stable both at room temperature and at 45° C. over three weeks without visible phase separation)

BACKGROUND

In addition to cleaning, another highly desirable characteristic of personal cleanser/shower gel type compositions is to deliver consumer perceivable (e.g., sensory or visual) benefits from the compositions to the skin. One important way of achieving this result is through deposition of benefit agent (e.g., emollient oils and/or of surfactant-insoluble inorganic particles). In turn, this may require incorporation of high levels of such oil or inorganic particles into the cleanser/shower gel composition.

Unfortunately, such dual cleansing and moisturizing compositions are difficult to formulate because cleansing ingredients, in general, tend to be incompatible with moisturizing ingredients. For example, emulsified oil droplets, especially hydrocarbon oil droplets, tend to phase separate from liquids during storage and to form a separate layer at the top of the liquid cleanser.

Also, emollient oils often tend to depress foaming/lathering of cleansing ingredients, especially when the level of surfactants in the liquid cleanser is relatively low (e.g., below about 25% by wt.). However, liquid cleansers containing relatively low level of surfactants and having good lather properties are highly desired because the lower surfactant levels tend to make the composition more mild, to lower cost and to facilitate processing.

Accordingly, there is a need in the art for compositions which contain low level of cleansing ingredients, which are both mild and capable of producing abundant lather, and which also can deliver moisturizing or other active ingredients. In addition, such compositions should stay physically stable at both ambient and elevated storage temperature.

Liquid cleansers, which can deliver skin benefit agents to provide some kind of skin benefit, are known in the art. For example, one method of enhancing delivery of benefit agent to the skin or hair is using cationic polymers such as Polymer JR® from Amerchol or Jaguar® from Rhone Poulenc. This method is disclosed, for example, in U.S. Pat. No. 3,580,853 to Parran et al, U.S. Pat. No. 5,085,857 to Reid et al., U.S. Pat. No. 5,439,682 to Wivell et al; or in WO 94/03152 (assigned to Unilever), WO 92/18100 (assigned to Procter & Gamble) or WO 97/48378 (assigned to Procter & Gamble).

Another method of enhancing delivery of benefit agents to the skin or hair is using large droplets of viscous oils as is described in U.S. Pat. No. 5,661,189 to Grieveson (assigned to Unilever) and U.S. Pat. No. 5,854,293 (assigned to Procter & Gamble).

In addition, the art discloses that physical stability of, for example, an emollient oil cleanser system requires the presence of some sort of suspending or stabilizing agent. U.S. Pat. No. 5,308,526 to Dias et al and U.S. Pat. No. 5,439,682 to Wivell et al, for example, teach the use of crystalline ethylene glycol long chain esters (e.g., ethylene glycol distearate) as suspension agents to prevent the separation of oil droplets from the liquid. There is no disclosure of a water soluble or water swellable starch as a structuring system to provide enhanced stability.

Another type of well-known suspension agents used to stabilize oil droplets in liquid cleansers are high molecular weight, water-soluble polymers such as polyacrylate, modified celluloses and guar polymers as disclosed broadly, for example, in U.S. Pat. No. 5,661,189 to Grieveson et al. and U.S. Pat. No. 5,854,293 to R. W. Glenn, Jr. (assigned to Procter & Gamble). These polymeric stabilizers are also specifically described, for examples, in U.S. Pat. No. 5,905,062 to Elliott et al. (P&G) claiming hydrophobically modified nonionic cellulose for liquid stability, in U.S. Pat. No. 6,172,019 B1 to Dehan et al. (Colgate-Palmolive) using combination of two separate polyacrylic acid polymers and in U.S. Pat. No. 6,001,344 to Villa et al. (Unilever) using the combination of xanthan gum and Carbopol® as a novel structuring system for stable liquid cleansing composition.

Without imparting negative effects on important cleanser properties (such as appearance, lather, in-use/after-use sensory properties and its processability), applicants have found that storage stable liquid cleansers containing emollient oils, fluid or particles, (e.g., 1 to 30% by wt.) can be formulated using a structuring system comprising specific water soluble/or swellable starch of a level higher than 5 wt. % (e.g., about 6 to 30%) in the liquid composition. Using starch structuring system as described in this invention, personal liquid cleansers with non stringy, non lumpy appearance, lotion-like rheology, excellent lather and storage stability can be easily formulated.

BRIEF DESCRIPTION OF THE INVENTION

Specifically, the application relates to stable, personal product (e.g., personal wash or hair) liquid cleansing compositions comprising (by wt.):

(1) 2 to 30%, preferably 3 to 25%, more preferably 5 to 20% by wt. of a surfactant selected form the group consisting of anionic surfactants, nonionic surfactants, amphoteric surfactants, cationic surfactants or mixtures thereof;

(2) 0 to 30%, (e.g., optional) preferably 0.5 to 20% skin benefit agent (e.g., emollient oil or benefit agent particle); and (3) about 6 to 30% modified or non-modified starch; wherein the pH of said composition is 4.0 to 9.0, preferably 4.5 to 8.0; and wherein said composition is stable at both room temperature and 45° C. for over 3 weeks with no visible phase separation.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to personal product (e.g., personal wash) liquid cleanser compositions which preferably comprise an emollient oil and/or particles and are very stable. Moreover, stability is not provided at the expense of lumpy looking and/or slimy-feeling compositions. Specifically, the use of starches in defined ranges (i.e., 6 to 30% by wt.) provides a structuring system yielding stability while avoiding product negatives.

Specifically, the composition provides:

(1) 2 to 30%, preferably 3 to 25%, more preferably 5 to 20% by wt. of a surfactant selected form the group consisting of anionic surfactants, nonionic surfactants, amphoteric surfactants, cationic surfactants or mixtures thereof;

(2) 0 to 30%, preferably 0.5 to 20% skin benefit agent (e.g., emollient oil or benefit agent particle); and (3) about 6 to 30% modified or non-modified starch;

wherein the pH of said composition is 4.0 to 9.0, preferably 4.5 to 8.0; and wherein said composition is stable at both room temperature and 45° C. for over 3 weeks with no visible phase separation.

The composition is defined in greater detail below:
Surfactant System
Anionic Surfactants The anionic surfactant may be, for example, , an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 0.5, preferably between 1 and 3; and M is a solubilizing cation such as sodium, potassium, ammonium or substituted ammonium. Ammonium and sodium lauryl ether sulfates are preferred.

The anionic may also be an alkyl glycinate, such as potassium cocoyl glycinate, an alkyl glutamate, such as potassium cocoyl glutamate; alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation; amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ(R) by Seppic.

Another surfactant which may be used are the $C_8$–$C_8$ acyl isethionates. These esters are prepared by reaction between alkali metal isethionate with mixed aliphatic IS fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

The anionic surfactant may also be a salt of $C_8$–$C_{22}$ carboxylic acid (also known as fatty acid soap). The fatty acid soap is known to be more irritative to skin than other mild anionic surfactants, such as potassium cocoyl glycinate. As such, the skin cleansing formulations claimed by this invention generally will comprise less than 10 %, preferable less than 6% said salt of fatty acid in the liquid cleanser composition of the invention. Preferably, the soaps used are straight chain, saturated $C_{10}$ to $C_{18}$ fully or partially neutralized fatty acids.

In general the anionic component will comprise from about 1 to 25% by weight of the composition, preferably 2 to 15% by weight of the composition.
Zwitterionic and Amphoteric Surfactants Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

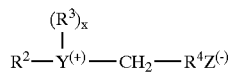

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropyl-ammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[Sethyl-S-(3dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

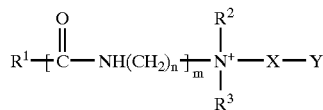

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

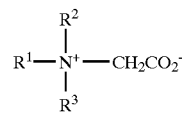

and amido betaines of formula:

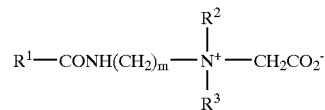

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

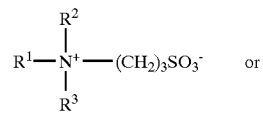 or

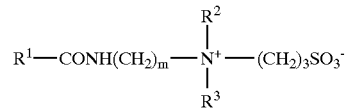

where m is 2 or 3, or variants of these in which —$(CH_2)_3$$SO^-_3$ is replaced by

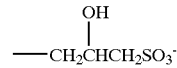

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5 to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in Patent No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

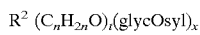

$$R^2 (C_nH_{2n}O)_t(glycOsyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The total surfactants in the liquid cleanser composition can be in the range of 2 to 30 wt. %, preferably 3 to 25%, most preferably 5 to 20%. For good lather, the combination of anionic surfactants and amphoteric/zwitterionic surfactants is preferably more than 40 wt % of the total surfactants, most preferably more than 60 wt. % of the total surfactant in the liquid cleanser composition of this invention.

Starches Granules (Stabilizing/Thickening Agent)

The key component of the liquid personal cleanser composition of the invention is the thickening/ stabilizing system. The thickening/stabilizing system of this invention is a modified or non-modified starch granule. This novel thickening/ stabilizing system works for a wide range of synthetic surfactants and liquid cleansers and allows compositions to have a viscosity ranging from pourable to lotion-like which can be easily formulated simply by changing the amount of starch added into the system.

Other than thickening/stabilizing the personal liquid composition, the starch stabilizing system also helps the lather properties of synthetic surfactants. For example, cleansers containing this novel thickening/stabilizing system produce creamier lather than a cleanser without the novel stabilizing system of this invention.

The starches of the invention are high molecular weight polysaccharides derived from plants such as corn, waxy corn, topioca, potato, wheat or rice. Plants synthesize starch and accumulate it in small discrete particles, called starch granules, having a size in the range of 1 to 100 micrometers depending on the source of plant. Non modified starch granules are insoluble in water at a temperature below 40° C. Starch can work as a thickening or structuring agent only after the starch granules are dissolved or are highly swollen by water. This can be achieved either by heat or by physical or chemical modification of the starch granules.

The temperature that is required to dissolve or to fully swell the starch granules varies with the plant source or the modification, if any, of a particular starch. For non modified starch granules, in general, potato starch gelatinizes at a lower temperature (around 65° C.) than waxy maize starch (around 70° C.) which, in turn, gelatinizes at a lower temperature than regular corn starch (around 75° C.). The gelatinization temperature (a critical temperature above which the intermolecular hydrogen bonds holding the granule together are weaker and the granule undergoes a rapid irreversible swelling by water) of a starch granule can be dramatically reduced by physically or chemically modifying the starch granule to make them suitable for low temperature processing. For example, Pure-Gel® Starches from Grain Processing Corporation are chemically modified corn starch granules having a gelatinization temperature around 53° C. which is well below the gelatinization temperature of a non-modified corn starch, which is around 75° C.

Modified or non-modified starch granules with gelatinization temperature between 30° to 85° C., preferably 30° to 70° C. are most preferred as the thickening/structuring agent of this invention. These types of starch granules are easy to process. It can be handled as a concentrate aqueous slurry (30 to 60% solids) which is flowable and pumpable at room temperature with until the slurry is heated to a temperature above its gelatination temperature.

In the subject invention, swelling or dissolution of starch granules can be done either, with or without the presence of surfactants, at a temperature higher than the gelatinization temperature of the specific starch granule. Higher processing temperature, in general, produces liquid cleansers with higher viscosity or better suspension properties due to higher swelling or better solubilization of these starch granules. It is preferred to process the starch granule in the presence of surfactants. In the presence of surfactants, these starch granules swell to form starch gel particles after being processed at a temperature higher than its gelatinization temperature to thicken, structure and stabilize the liquid cleanser composition of this invention. Due to the way the liquid cleanser is stabilized by the swollen starch gel particles, the liquid cleanser of this invention has very shear thinning rheology, non stringy, non lumpy smooth appearance, and is easy to disperse in water during the use of the product.

In general, whatever starch is used, it is preferred that the starch granule, upon use in the final composition, swell at least 200% by volume, preferably at least 400%, more preferably at least 600%, and most preferably at least 800% by volume to form swollen starch gel particles with size in the range of 2 to 300 micrometers.

Examples of modified or non modified starch granules which require heat to swell or to dissolve to thicken the liquid cleanser composition of the invention are PureGel B990, PureGel B992, PureGel B980 or PureDent starches from Grain Processing. Examples of other commercially available starches granules are National 1545, Amioca corn starch, Structure Soaln (a modified potato starch), Clearjel, Hi Flo, National 1333, Colflo 67, National Frige, Novation 1600, Novation 2700 or Purity 420 from National Starch and Chemical Company. Chemically modified starch granules are preferred. Especially, starch granules modified with nonionic hydrophilic groups such as hydroxylethyl or hydroxypropyl and/or ionic groups such as phosphate, carboxylate, sulfate, sulfonate and dialkyl/trialkyl amino or quaternary ammonium ion are highly preferred. Aqueous solution of starches, especially those containing amylose molecules, tend to form aggregates with lumpy appearance during aging of the product. The stability problem of starch containing aqueous solutions can be prevent or minimized by modification of starch granules with nonionic and/or ionic hydrophilic groups. Other than better stability, the gelatinization temperature of the starch can be reduced dramatically by the level of hydrophilic groups attached to the starch molecules. In general, the gelatinization temperature decreases with increasing level of s substitution. At high degree of substitution, the chemically modified starch granule becomes swellable in cold-water.

Modified starch granules, especially hydroxypropyl starch phosphate granules with gelatinization temperature in the range of 30 to 70° C., such as PureGel starches, are highly preferred.

Other than starch granules described above, there are pregelatinized cold water soluble starches which disperse and dissolve easily in cold water without the need of heating. These cold water soluble starches have been gelatinized and dried, so they will is disperse and swell in cold water. Examples of pregelatinized cold water soluble starches are Ultra-Sperse tapioca or waxy maize starch, Stir-N-set tapioca starch, National 5717 pregelatinized modified waxy maize starch, National 1215 pregelatinized unmodified corn starch, Structure ZEA, a hydroxypropyl modified corn starch or Structure XL, a cross-linked pregelatinized hydroxypropyl starch phosphate. All the starches mentioned above are commercially available from National Starch and Chemical Company. Cold water soluble starches can also be used in this invention. However, it is not preferred to use these alone as the thickening agent for the liquid cleanser composition of the invention. Liquid cleanser composition thickened with only pregelatinized cold-water soluble starch, such as Unltra-Sperse A or Structure XL, becomes lumpy after being aged at RT for over 3 weeks. The cold water soluble starch, if used, should be combined with the starch granules described above or with other water soluble polymer such as xanthan gum, carbopol, hydroxyethyl cellulose, hydroxypropylmethyl cellulose, hydrophobically modified hydroxy ethyl cellulose, or hydrophobically modified carbopol® to produce a stable, non lumpy liquid cleanser composition.

Depending on the processing temperature, the starch thickening efficiency, the amount and composition of surfactants used in the cleanser, the pH of the liquid, the additives in the liquid cleanser composition and the desired final liquid viscosity, the amount of modified and/or nonmodifed starch granules in the liquid can be in the range of 6 to 30 wt. %, preferably 6 to 25 wt. % of the composition. The final viscosity of the liquid should be in the range of 10 to 400 Pascal, preferably in the range of 20 to 300 Pascal, most preferably in the range of 40 to 200 Pascal at 1 $sec^{-1}$ when measured at 25° C. using Haake RV20 Rotovisco Rheometer with SV1ST spindle. If the viscosity is lower than 10 Pascal, the prepared composition is not stable at room temperature and the starch gel particle precipitates out of the composition to form separate gel phase at the bottom of the liquid. If it is higher than 400 Pascal, the liquid is too pasty to process and to disperse easily during the use of the product.

Skin Benefit Agent

The optional skin benefit agents which may be used in starch structured liquid compositions of the invention are defined as cosmetic grade organic, inorganic or polymeric materials that are not soluble (i.e., less than 1% soluble in the liquid composition) in the liquid cleanser composition. Examples of the benefit agent may comprise various classes of oils are as set forth below:

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and avocado oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acetylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include natural or synthetic wax , aloe vera, mineral oil, petrolatum, and polymeric benefit agent such as dimethyl polysiloxane, silicone elastomer, hydrogenated or non-hydrogenated polymers of alkylene or isoalkylene like polybutenes, polyalphaolefines, polyeaters or polyacrylates, and mixture of above The agent may also include inorganic particles such as non-modified or modified mica, silica, talc and titanium dioxide.

The skin benefit agent (e.g., emollient oil), if used, is generally in an amount from about 0.1 to 30%, preferably 0.5 to 20% by wt. of the composition.

Particle size of the benefit agent can be in the range of 0.01 up to 500 micrometers, preferable 0.1 to 200 micrometers.

In addition, the compositions of the invention may include optional ingredients as follows:

Water-soluble skin benefit agent, an essential optional ingredient that is preferred to be included in the liquid composition. A variety of water-soluble skin benefit agents can be used and the level can be from 1 to 30 weight %, preferably 1 to 20% by wt. Skin conditioning effect of deposited oils can be enhanced by addition of these water-soluble skin benefit agents. The materials include, but are not limited to, polyhydroxy alcohols such as glycerol, propylene glycol, sorbitol, pantenol and sugar; urea, alphahydroxy acid and its salt such as glycolic or lactic acid; and low molecular weight polyethylene glycols with molecular weight less than 20,000. Preferred water soluble skin benefit agents for use in the liquid composition are glycerol, sorbitol and low molecular weight polyethylene glycols.

Cationic polymer, another highly desirable optional ingredient may be used in the composition to provide the preferred skin feel and to enhanced the deposition of skin benefit agent with particle size less than 10 micrometers. Examples of cationic polymers are modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series.by Henkel, Inc.;

Quadrosoft Um-200; and Polyquatemium-24.

Auxiliary thickeners, such as carboxymethylcellulose, magnesium aluminum silicate, hydroxyethylcellulose, hydrophobically modified hydroxy ethyl cellulose, hydroxypropylmethylcellulose, carbopols, hydrophobically modified carbopols, xanthan gum, polyacrylate, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, TiO$_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy4,2'4' trichlorodiphenylether (DP300); preservatives such as dimethyloldimethylhydantoin (Glydant XL 1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut sheets and apricot seeds and solid inorganic particles such as Talc and silicate. Capsules like perfume capsules or oil capsules can also be used.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES 1–7

Effect of Starch Level Land Surfactant Composition on Liquid Stability

TABLE 1

| | | | | Example | | | |
|---|---|---|---|---|---|---|---|
| | 1 | 2 | 3 | 4 (Comparative) | 5 | 6 | 7 (Comparative) |
| Sodium lauroamphoacetate | 7.6 | 7.6 | 7.6 | 7.6 | — | — | — |
| Sodium N-cocoyl N-methyl taurate | — | — | — | — | 2.85 | 2.85 | 2.85 |
| Potassium cocyl glycinate | 9.5 | 9.5 | 9.5 | 9.5 | 14.25 | 14.25 | 14.25 |
| Lauric acid | 1.9 | 1.9 | 1.9 | 1.9 | 1.9 | 1.9 | 1.9 |
| Glycerin | 6 | 6 | 6 | 6 | 6 | 6 | 6 |
| Starch (PureGel B990 ex. Grain Processing) | 18 | 12 | 8 | 5 | 18 | 16 | 12 |
| Merquat 100 | .020 | .020 | .020 | .020 | .020 | .020 | .020 |
| Jaguar C13S | 0.05 | 0.05 | 0.05 | 0.05 | 0.10 | 0.05 | 0.05 |
| TiO2 | 0.30 | 0.30 | 0.30 | 0.30 | 0.10 | 0.30 | 0.30 |
| Petrolatum | 3.75 | 3.75 | 3.75 | 3.75 | 2.25 | 2.25 | 2.25 |
| Polybutene (Indopol H1500 ex. Amoco) | 1.25 | 1.25 | 1.25 | 1.25 | 0.75 | 0.75 | 0.75 |
| Glydant plus | 0.20 | 0.20 | 0.20 | 0.20 | 0.20 | 0.20 | 0.20 |
| EDTA | 0.05 | 0.05 | 0.05 | 0.05 | 0.05 | 0.05 | 0.05 |
| Perfume | 0.25 | 0.25 | 0.25 | 0.25 | 0.25 | 0.25 | 0.25 |

All the examples were prepared by first mixing deionized water, surfactants and starch in a 70 to 75° C. water bath for 10 to 15 minutes to swell or dissolve the starch granules or powders. A premix of emollient oil emulsions, i.e., petrolatum and polybutene emulsion, Merquat 100, Talc and TiO$_2$ was prepared and added to the reactor and mixed for another 10 minutes at 70 to 75° C. Glycerine, lauric acid and Jaguar C13S were premixed at 70° C. to melt lauric acid. The premix was then added to the reactor and mixed for 10 minutes at 70 to 75° C. Calculated amount of sodium hydroxide or citric acid solution was then added to adjust the pH of the liquid. The liquid was then cooled at cold water bath. The rest of ingredients such as Glydant plus, EDTA, mica and perfume were added during the cooling of the liquid cleanser composition. After the liquid was cooled below 35° C., pH was measured and adjusted with either KOH or citric acid solution to the range of 6.8 to 7.0. Petrolatum/polybutene emulsion was prepared by first mixing petrolatum and polybutene at 70° C. until it formed a uniform mixture. The petrolatum/polybutene premix was then mixed with equal amount of 5 wt. % Na laurel (2)ethoxysulfate solution at high shear to form the emulsion with more than 60 wt. % of petrolatum/polybutene having a size in the range of 0.5 to 10 micrometers. All the liquid compositions shown in Table 1 except Example 4 and Example 7 had a viscosity higher than 30 Pascal at 1 sec$^1$ at 25° C. and are stable at both 45° C. and RT for over 30 days. Two comparative examples, Examples 4 and 7, with a viscosity lower than 20 Pascal at 1 sec$^1$ at 25° C. showed phase separation with a clear layer at the top of the liquid after storage at room temperature for 3 weeks. As shown in these examples, the amount of starch required to stabilize the liquid cleanser depends on the surfactant composition. Example 3 containing sodium lauryl amphoacetate (Example 3) is much more stable than the one with sodium N-cocyl N-methyl taurate (Example 7) even at a lower level of starch.

EXAMPLES 8–16

Effect of Surfactant Composition

TABLE 2

| | Example | | | | | | | | |
|---|---|---|---|---|---|---|---|---|---|
| | 8 | 9 | 10 | 11 | 12 | 13 | 14 | 15 | 16 |
| Sodium N-cocoyl N-methyl taurate | 2.85 | 2.25 | — | — | — | — | — | — | 3.0 |
| Sodium lauroamphoacetate | — | — | — | 3.9 | — | 5.7 | 5.7 | — | — |
| Sodium lauryl sulfosuccinate | — | — | 7.6 | — | 5.7 | — | — | — | — |
| Potassium cocoyl glycinate | 16.2 | 11.25 | 9.5 | 7.8 | 7.6 | 5.7 | 5.7 | 9.5 | — |
| Sodium lauryl 2 ethoxylated sulfate | — | — | — | — | 3.8 | — | — | — | — |
| Alkylpolyglucoside (Plantan 2000) | — | — | — | — | — | — | 5.7 | 5.7 | — |
| Potassium monolauryl phosphate | — | — | — | — | — | 5.7 | — | — | — |
| Potassium mono C16 phosphate | — | — | — | — | — | — | — | 1.9 | — |
| Lauric acid | — | 1.5 | 1.5 | 1.3 | 1.5 | 1.9 | 1.9 | 1.9 | — |
| Potassium laurate | — | — | — | — | — | — | — | — | 6.0 |
| Glycerin | 6 | 6 | 6 | 20 | 6 | 6 | 6 | 6 | 6.0 |
| PureGel B990 | 18 | 18 | 12 | 14 | 14 | 12 | 16 | 12 | 18.0 |
| Merquat 100 | 0.20 | 0.20 | 0.20 | 0.20 | 0.20 | 0.20 | 0.20 | 0.20 | 0.40 |
| Jaguar C13S | 0.10 | 0.05 | 0.05 | 0.05 | 0.05 | 0.05 | 0.05 | 0.05 | — |
| TiO2 | 0.5 | 2.5 | 2.5 | — | 0.2 | 0.2 | 0.2 | 0.2 | 3.0 |
| Mica MP30 from Rona | 0.15 | 0.15 | 0.15 | — | — | — | — | — | — |
| Soft Talc | 2.0 | 2.0 | 2.0 | — | — | — | — | — | 2.0 |
| Petrolatum | 2.25 | 2.25 | 3.75 | 2.25 | 3.75 | 3.75 | 3.75 | 3.75 | 3.75 |
| Polybutene (Indopol H1500) | 0.75 | 0.75 | 1.25 | 0.75 | 1.25 | 1.25 | 1.25 | 1.25 | 1.25 |
| Glydant plus | 0.20 | 0.20 | 0.20 | 0.20 | 0.20 | 0.20 | 0.20 | 0.20 | 0.20 |
| EDTA | 0.05 | 0.05 | 0.05 | 0.05 | 0.05 | 0.05 | 0.05 | 0.05 | 0.05 |
| Perfume | 0.25 | 0.25 | 0.25 | 0.25 | 0.25 | 0.25 | 0.25 | 0.25 | 0.25 |

Examples 8 to 16 show that the starch polymer is robust and works for a wide range of surfactant compositions and surfactant level. All the examples were prepared using the same method described in Examples 1–7. The pH of Examples 8 to 15 is in the range of 6.8 to 7.0. The pH for Example 16, which contains mixture of lauric acid soap and a synthetic surfactant is in the range of 8.5 to 8.8. All the examples shown in Table 2 are stable at both 45° C. and room temperature for over 3 weeks.

EXAMPLES 17–23

Effect of Emollient Oils and Starches

TABLE 3

| | Example | | | | | | |
|---|---|---|---|---|---|---|---|
| | 17 | 18 | 19 | 20 | 21 | 22 | 23 |
| Sodium lauroamphoacetate | 7.6 | 7.6 | 5.7 | 5.7 | 5.7 | 5.7 | 5.7 |
| Potassium cocoyl glycinate | 9.5 | 9.5 | 11.4 | 11.4 | 11.4 | 11.4 | 11.4 |
| Lauric acid | 1.7 | 1.7 | 1.7 | 1.7 | 1.7 | 1.7 | 1.7 |
| Glycerin | 6 | 6 | 6 | 6 | 6 | 6 | 6 |
| PureGel B990 starch (ex. Grain Processing) | 12 | 12 | 12 | — | — | — | 8 |
| National 1545 starch (ex. National Starch & Chemical) | — | — | — | 14 | — | — | — |
| Amioca Corn starch (ex. National Starch & Chemical) | — | — | — | — | 14 | — | — |
| UltraSperse A starch (pregelatinized starch, ex. National Starch & Chemical) | — | — | — | — | — | 12 | 4 |
| Merquat 100 | .020 | .020 | .020 | .020 | .020 | .020 | .020 |
| Jaguar C13S | 0.05 | 0.05 | 0.05 | 0.05 | 0.05 | 0.05 | 0.05 |
| TiO2 | 0.30 | 0.30 | 0.30 | 0.30 | 0.30 | 0.30 | 0.30 |
| Petrolatum | — | — | 8.0 | 3.75 | 3.75 | 3.75 | — |
| Polybutene (Indopol H1500) | — | — | — | 1.25 | 1.25 | 1.25 | — |

TABLE 3-continued

| | Example | | | | | | |
|---|---|---|---|---|---|---|---|
| | 17 | 18 | 19 | 20 | 21 | 22 | 23 |
| Silicone oil (Dow Corning 1785) | 5 | — | — | — | — | — | 6 |
| Sunflower seed oil | — | 5 | — | — | — | — | — |
| EDTA | 0.05 | 0.05 | 0.05 | 0.05 | 0.05 | 0.05 | 0.05 |
| Perfume | 0.25 | 0.25 | 0.25 | 0.25 | 0.25 | 0.25 | 0.25 |
| Processing temperature | 70–75° C. | 70–75° C. | 70–75° C. | 80–85° C. | 80–85° C. | 70–75° C. | 70–75° C. |

Examples 17 to 23 show effect of emollient oils and starches on liquid cleanser properties of this invention. All the examples were prepared using the method described in Example 1–7 except Examples 20 and 21, which were processed at 80 to 85° C. instead of 70–75° C. All the examples are stable at both 45° C. and room temperature for over 3 weeks except Example 22. Example 22 is stable at room temperature. However, it became lumpy appearance after storage at room temperature for over 3 weeks. UltraSperse A used in Example 22 is a cold water soluble pregelatinized waxy maze starch. In the liquid cleanser composition, this starch formed soluble starch instead of swollen starch gel particles like PureGel B990, National 1545 or Amioca Starch. The lumpy appearance of Example 22 is believed due to the aggregation of the soluble UltraSperse A starch during storage. This lumpy appearance problem could b solved by using combination of UltraSperse A and a starch granule like Pure Gel B1990 as shown in Example 23.

EXAMPLE 24

Lather Evaluation

The lather properties of Examples 8, 9 and 10 prepared above were evaluated by a trained sensory panel which comprised 20 panelists, female with ages between 33 to 55 years old. A non-starch stabilized liquid cleanser was used as the comparative example in the panel study. The comparative example contains mainly 17% Na cocyl glycinate, 0.6% Na cocylmethyltaurate, 0.9% cocamidopropylbetaine, 2.7% Na laurylamido diacetate, 1.5% stearic acid, 2.5% ethyleneglycol distearate, 21.67% glycerin, 1.0% polyoxyethylene 20EO cetylether and 0.18% polyacrylic acid. The panel results are summarized in Table 4. Higher mean score indicates more or better for each sensory attribute. As shown in the table, all starch stabilized liquid cleanser compositions of this invention (Example 8, 9 and 10) have better lather properties than the comparative example. All 3 liquid cleanser composition of this invention were perceived more creamy (smaller bubble size and whiter appearance) and had better lather consistency and lather stability than the comparative example.

TABLE 4

Mean scores of lather attributes

| | Example 8 | Example 9 | Example 10 | Comparative Example |
|---|---|---|---|---|
| Amount of small bubble* | 23 | 25 | 30 | 14 |
| Amount of large bubble* | 5 | 4 | 3 | 9 |
| Lather consistency | 25 | 29 | 29 | 15 |

TABLE 4-continued

Mean scores of lather attributes

| | Example 8 | Example 9 | Example 10 | Comparative Example |
|---|---|---|---|---|
| Bubble whiteness | 31 | 32 | 30 | 28 |
| Bubble stability | 28 | 24 | 30 | 17 |

*higher score of "amount of small bubble" and lower score of "amount of large bubble" mean more creamy lather.

What is claimed is:

1. A personal wash liquid cleansing compositions comprising (by wt.):
    (1) 2 to 30% by wt. of a surfactant selected from the group consisting of anionic surfactants, nonionic surfactants, amphoteric surfactants, cationic surfactants or mixtures thereof;
    (2) a structuring system comprising about 6 to 30% total composition modified or non-modified starch granules, wherein said starch granules are modified or non-modified granules having a gelatinization temperature in the range of 30° to 85° C.; and
    (3) 0 to 30% benefit agent;
    wherein the pH of said composition is 4.0 to 9.0;
    wherein said composition is stable at both room temperature and 45° C. for over 3 weeks with no visible phase separation;
    wherein final viscosity of the liquid is in the range 10 to 500 Pascal at 1 sec$^{-1}$ when measured at 25° C. using Haake RV20 Rotovisco Rheometer; modified starch referring to physical or chemical modification to enhance dissolution or swelling of starch in water.

2. A composition according to claim 1, comprising 3 to 25% by wt. surfactant.

3. A composition according to claim 1, comprising 5 to 20% by wt. surfactant.

4. A composition according to claim 1, wherein the starch granule, upon use said liquid cleanser composition, has a gel particle size in the range of 2 to 300 micrometers.

5. A composition according to claim 1, wherein the starch granule, upon use said liquid cleanser, swells at least 200% by volume.

6. A composition according to claim 1, wherein the starch granules are chemically modified with ionic and/or nonionic hydrophilic group or groups to have a gelatinization temperature in the range of 30° to 75° C.

7. A composition according to claim 5, wherein the ionic or nonionic groups are selected from hydroxylpropyl, hydroxyethyl, phosphate, sulfonate, sulfonata, carboxylate, dialkyl/trialkyl amino, quaternary ammonium, and mixtures thereof.

8. A composition according to claim 1, wherein the pH of the liquid cleanser composition is in the range of 5.0 to 8.0.

9. A composition according to claim 1, wherein the viscosity of the said liquid composition is in the range of 20 to 300 Pascal at 1 sec$^{-1}$ when measured at 20° C. using Haake RV20 Rotovisco Rheometer.

10. A composition according to claim 1, comprising 0.5 to 20% benefit agent.

11. A composition according to claim 1, wherein benefit agent is a cosmetic grade organic, inorganic or polymeric material not soluble in liquid cleanser.

12. A composition according to claim 11, wherein not soluble is defined as less than 1 wt. % solubility of the active in the liquid cleanser composition.

* * * * *